(12) United States Patent
Gebicki et al.

(10) Patent No.: US 8,304,439 B1
(45) Date of Patent: Nov. 6, 2012

(54) USE OF QUATERNARY PYRIDINIUM SALTS AS A THERAPEUTIC OR PREVENTING AGENT AGAINST IONIZING RADIATION-INDUCED DAMAGE

(75) Inventors: Jerzy Gebicki, Lodz (PL); Andrzej Marcinek, Lodz (PL); Stefan Chlopicki, Cracow (PL); Marek K. Janiak, Warsaw (PL)

(73) Assignees: Politechnika Lodzka, Lodz (PL); Uniwersylet Jagiellonski, Krakow (PL)

( * ) Notice: Subject to any disclaimer, the term of this patent is extended or adjusted under 35 U.S.C. 154(b) by 1063 days.

(21) Appl. No.: 12/287,664

(22) Filed: Oct. 9, 2008

Related U.S. Application Data

(60) Provisional application No. 61/010,487, filed on Jan. 9, 2008, provisional application No. 60/998,856, filed on Oct. 12, 2007.

(51) Int. Cl.
*A61K 31/44* (2006.01)
(52) U.S. Cl. .............................. 514/358; 514/43; 514/89
(58) Field of Classification Search ................... 424/9.1; 514/43, 89, 358
See application file for complete search history.

(56) References Cited

U.S. PATENT DOCUMENTS

| 7,893,095 | B2 * | 2/2011 | Marcinek et al. ............. 514/358 |
| 2006/0160805 | A1 | 7/2006 | Ternansky et al. |

FOREIGN PATENT DOCUMENTS

| WO | 2005067927 | 7/2005 |
| WO | 2007074406 | 7/2007 |
| WO | 2007103540 | 9/2007 |
| WO | 2008104920 | 9/2008 |

OTHER PUBLICATIONS

Allen J.B. et al., "Irradiation decreases vascular prosyacyclin formation with no concomitant effect on platelet thromboxane production", Lancet, vol. 2, No. 8257, (Nov. 1981), pp. 1193-1196.
Milas et al., "Cyclooxygenase-2 (COX-2) enzyme inhibitors as potential enhancers of tumor radioresponse", Seminars in Radiation Oncology, Suanders, Philadelphia, PA, US, vol. 11, No. 4, Oct. 1, 2001, pp. 290-299.
International Search Report issued by the International Searching Authority (ISA/EP) on Feb. 26, 2009 in connection with International Application No. PCT/EP2008/063534.

* cited by examiner

*Primary Examiner* — Michael G Hartley
*Assistant Examiner* — Jagadishwar Samala
(74) *Attorney, Agent, or Firm* — Gary J. Gershik; Cooper & Dunham LLP

(57) ABSTRACT

A method for the treatment or prevention of a cell or tissue damage in a living subject due to the exposure to ionizing radiation is provided, which comprises administration to said subject of a compound of formula (I) wherein R' is H, OH, $CONH_2$ or $COCH_3$, R" is H or $CH_3$, R''' is H or $CH_3$, and $X^-$ is a pharmaceutically acceptable counterion, in an amount sufficient to inhibit radiation-induced damage.

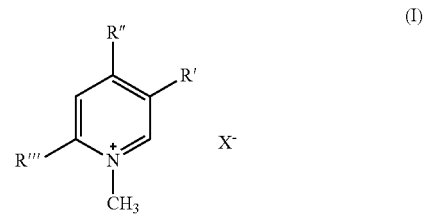

19 Claims, 2 Drawing Sheets

USE OF QUATERNARY PYRIDINIUM SALTS AS A THERAPEUTIC OR PREVENTING AGENT AGAINST IONIZING RADIATION-INDUCED DAMAGE

RELATED APPLICATIONS

This application claims benefit of U.S. Provisional Application No. 61/010,487, filed on Jan. 9, 2008 and of U.S. Provisional Application No. 60/998,856, filed on 12 Oct., 2007, the entire contents of which are hereby incorporated herein by reference in their entirety.

THE FIELD OF THE INVENTION

The present invention relates generally to the field of radioprotection, including radioprotection in a radiotherapy (radiation therapy). In particular it relates to a method for the treatment or prevention of a cell, tissue or organ damage in a living subject caused by the exposure to the ionizing radiation of any type. The method of the invention comprises administration of effective amounts of certain quaternary pyridinium salts to a subject, including human.

THE STATE OF THE ART

Ionizing radiation, i.e. the radiation with the energy high enough to have the potential of the ionization of molecules in a living body, may cause serious damages and injuries to the cells and tissue of living beings. Ionizing radiation damages tissue by direct ionization, which disrupts molecules directly and also by producing highly reactive free radicals, which attack nearby cells. The net effect is that biological molecules suffer local disruption; this may exceed the body's capacity to repair the damage and may also cause mutations in cells currently undergoing replication. In consequence, a dysfunction of many important organs, and even multiple organ failure is observed, which can eventually lead to a death (radiation-induced lethality). Damaging and harmful effects of the radiation can be observed both in the case of acute high dose exposure or in the case of chronic exposure to lower doses. These include so called radiation sickness caused by chronic exposure to the radiation emitting environment, and radiation sickness (poisoning), caused by acute exposure to the internal or external action of a radioactive material or a source of radiation.

Chronic exposure to low doses has mutagenic activity and brings a risk of developing cancer. Harmful effects of the radiation can be also due to the exposure of a patient or a medical staff to the radiation during routine radiodiagnostic procedures or a radiotherapy, like radiotherapy of a cancer, where radiation which destroys cancer cells can at the same time damage healthy, normal cells.

Some agents have been approved for eliminating radioactive substances from the body, among them radiogardase (prussian blue), pentetate calcium trisodium (Ca-DTPA) and pentetate zinc trisodium (Zn-DTPA).

Chemicals capable of protecting the cells and tissue against harmful effects of the radiation, called radioprotectors, are used and tested in clinical trials. Among them aminothiol compounds, like mercaptamine, glutation, amifostine and their phosphorylated pro-drugs, have been developed. Aminothiole protectants exert their action due to their free-radicals scavenging and antioxidant ability and to provide effective protection must be given prior to the exposure.

The disadvantage and the main limitation of the classical aminothiol-based radioprotectors is their high toxicity, especially at concentrations required for radioprotection, low efficiency when used after the radiation exposure, lack of protection against radiation-induced lethality/mortality, and generally low degree of protection. In the case of cancer radiotherapy a potential disadvantage is a risk of compromising cancer cells kill when radioprotector reaches tumor cells.

In the recent years the interest in biological treatments which could be administered after the exposure could have been observed. This included the use of agents which could increase survival after accidental radiation injuries: anti-apoptotic proteins, cell growth factors, G-CSF and GM-CSF (filgrastim). These drugs stimulate the growth of white blood cells and can help repair bone marrow damage. They can be also used in patients receiving radiation therapy.

Due to extensive use and presence of ionizing radiation and/or radiation sources in many fields of human activity, such as medicine, nuclear power plants, industry, as well as the threat of contamination caused by nuclear/terrorist attacks the need still exists for radioprotectors based on simple chemical molecules, which could be effective especially in preventing radiation-induced lethality while being non-toxic and safe at concentrations required for effective protection. It is important as well that potential radioprotection candidate is relatively cheap and easy to manufacture.

The method of protection against radiation caused damage discovered by the present inventors employs simple and cheap small molecules—certain quaternary pyridinium salts.

Certain therapeutic uses of quaternary pyridinium salts are known.

In WO00/40559 therapeutic and cosmetic uses of 1,3-disubstituted pyridinium salts, including 1-methylnicotinamide (MNA) salts were disclosed. It was reported that said derivatives have the utility in topical treatment of skin diseases, in particular crural ulceration, acne, psoriasis, atopic dermatitis, vitiligo, as well as burns and scalds and in wound healing. Said derivatives have also the activity of promoting hair regrowth, therefore they are useful in the treatment of hair loss of different origin.

Effects of 1-methylnicotinamide chloride (MNA) in some skin diseases were described by Gębicki J, Sysa-Jędrzejowska A, Adamus J, Woźniacka A, Rybak M, Zielonka J. 1-Methylnicotinamide: a potent anti-inflammatory agent of vitamin origin. Pol J Pharmacol 2003; 55:109-112. It has been proposed that MNA displays anti-inflammatory action.

In WO2005/067927 the use of 1-methylnicotinamide and 1-methyl-3-acetylpyridinium salts as vasoprotective agents in the treatment of conditions and diseases associated with endothelial dysfunction was disclosed.

In Pharmacological Reports, 2007, 59, 216-223, studies of cytotoxic activity of selected pyridinium salts: 1-methylnicotinamide chloride, 1-methyl-3-acetylpyridinium chloride and 1-methyl-3-nitropyridinium chloride against murine leukemia L1210 were reported by the present inventors. It was found that the cytotoxicity in cultured leukemia cells varied strongly depending on the compound used and that 3-nitro-1-methylpyridinium chloride showed the highest cytotoxicity, while cytotoxicities of 1-methylnicotinamide chloride and 1-methyl-3-acetylpyridinium chloride were several thousands times lower, thus being in fact negligible. Furthermore, the activity of 1-methylnicotinamide chloride was observed only at very high concentration.

1-Methyl-3-acetylpyridinium salt (MAP$^+$) was described in a publication Takashi Sakurai, Haruo Hosoya. Charge transfer complexes of nicotinamide-adenine dinucleotide analogs and flavine mononucleotide. Biochim. Biophys. Acta 1966; 112(3):359-468.

SUMMARY OF THE INVENTION

The invention provides a method for the treatment or prevention of a cell, tissue or organ damage in a living subject caused by the exposure to a ionizing radiation, which method comprises administration to said subject of a compound of formula (I)

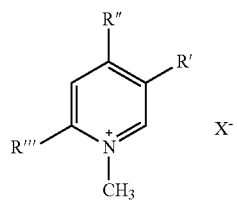

(I)

wherein R' is H, OH, CONH$_2$ or COCH$_3$, R" is H or CH$_3$, R'" is H or CH$_3$, and X$^-$ is a pharmaceutically acceptable counterion, in an amount sufficient to inhibit radiation-induced damage.

It has been unexpectedly found that the compounds of the above formula (I), while being devoid of any radical scavenging and antioxidant activity, possess the superior potential to protect living subjects against harmful effects of the ionizing radiation, including radiation sickness, radiation-induced lethality as well as harmful effects of radiotherapy to normal/healthy cells. Their superior effect can be observed after oral administration, although is much quicker after administration via parenteral route. The advantage which is very important especially in emergency cases is a quick onset of action. They show high efficiency when administered following the exposure to the ionizing radiation. The compounds of formula (I) are quickly redistributed in the body, do not accumulate during chronic/prolonged administration, and are devoid of side effects. Furthermore, they show efficiency in the case of the exposure to any type of ionizing radiation and in the case of both irradiation of a whole body of the living subject and particular organs of the body.

BRIEF DESCRIPTION OF THE DRAWINGS

The following drawings form part of the present specification and are included to further illustrate and demonstrate certain aspects of the present invention.

DETAILED DISCLOSURE OF THE INVENTION

Figure 1:
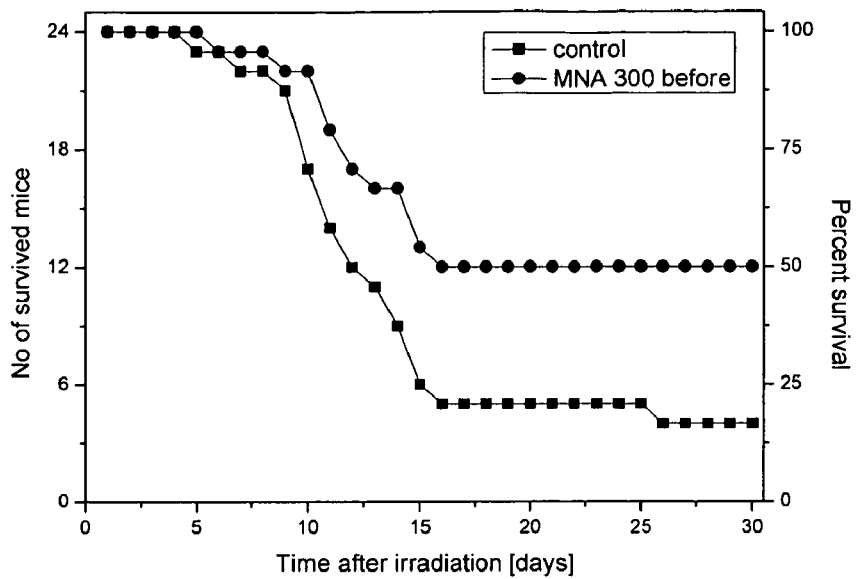
FIG. 1 shows the effect of the administration of 1-methylnicotinamide chloride (MNA) at 300 mg/kg/day before irradiation on the survival rate of mice after whole body irradiation with the dose of 7.5 Gy in comparison with the untreated group of mice. The influence of MNA given before irradiation at 300 mg/kg/day on the mice survival following the whole body irradiation with the dose of 7.5 Gy

The present invention provides a method for the treatment or prevention of a cell, tissue or organ damage in a living subject due to the exposure to a ionizing radiation, which method comprises administration to said subject of a compound of formula (I)

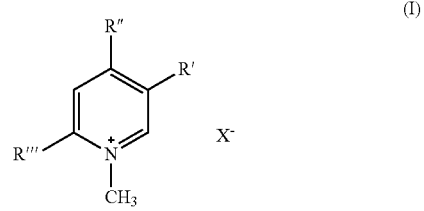

(I)

wherein R' is H, OH, CONH$_2$ or COCH$_3$, and R" is H or CH$_3$, R'" is H or CH$_3$, and X$^-$ is a pharmaceutically acceptable counterion, in an amount sufficient to inhibit radiation-induced damage.

As indicated above, in the compounds of formula (I) X$^-$ can be any pharmaceutically acceptable and physiologically suitable counter-anion. Said counterion is of a non-complex type, i.e. does not contain complexed metal cations. The quaternary pyridinium salts used in the method of the present invention can thus be derived from any physiologically suitable acceptable organic or inorganic acids. Suitable inorganic acid salts include, for example, chloride, bromide, iodide and carbonate. Suitable organic acid salts include for example mono-, di- and tri-carboxylic acid salts such as acetate, benzoate, salicylate, glycolate, lactate, maleate and citrate.

The method of the invention is useful in any types of the exposure, whether acute or chronic, to any type of ionizing radiation, whether natural or artificial.

The method of the invention can be also used prophylactically in the situations of the risk of the exposure to the radiation.

Said exposure to the ionizing radiation includes both routine (intentional)/expected and non-intentional/non-expected exposure.

In one embodiment of the method of the invention is used in the case of acute high-dose internal or external radiation exposure.

Acute high-dose exposure can be a result of an accident, such as for example an industrial accident, or an intentional act, such as nuclear weapon detonation, dirty bomb explosion, terrorist attack involving radioactive sources, and any other criminal act with the use of ionizing radiation or radioactive material. The exposure will be external when the radiation source acts from the outside of the body, as it is for example in the case of external radiotherapy (teletherapy). The exposure will be internal if the radioactive material is ingested or inhaled by a subject as it is for example in the case of internal radiotherapy (brachytherapy) or radiation poisoning.

In another embodiment of the method of the invention said exposure is a chronic low-dose internal or external radiation exposure.

In another embodiment of the method of the invention said exposure is during the radiotherapy, such as radiotherapy of a cancer or tumor.

One particular variant of this embodiment relates to the method where said exposure is during the radiotherapy, such as radiotherapy of a cancer or tumor, and said subject is a patient undergoing radiotherapy.

The additional advantageous effect can be seen in this variant of the method of the invention. Besides the effect of radioprotection of normal, healthy cells of said patient, the compounds of formula (I) exert also the effect of radiosensitization of abnormal cells, like tumor or cancer cells, in tissues subjected to the radiotherapy. Therefore in such variant of the invention the compounds of formula (I) provide both the radioprotecting and radiosensitizing effect. Due to this combined effect of the compounds of formula (I) the efficacy of radiotherapy can be increased or the same effect of the therapy at lower doses of the radiation can be achieved with lesser detrimental effects on healthy tissues.

Accordingly, there is also provided a method for the treatment of a cancer or tumor which comprises administration to a patient in need of such therapy of a compound of formula (I)

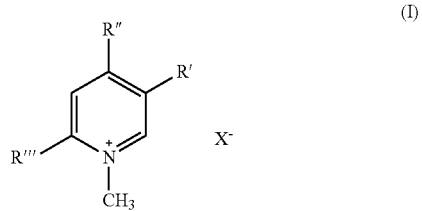

(I)

wherein R' is H, OH, $CONH_2$ or $COCH_3$, R" is H or $CH_3$, R''' is H or $CH_3$, and $X^-$ is a pharmaceutically acceptable counterion, in an amount sufficient to inhibit radiation-induced damage, and subjecting said patient to a radiotherapy.

There is also provided a method of performing a radiotherapy of a living subject in a need of such treatment which comprises administration to said subject before, during or following the radiotherapy of a compound of formula (I)

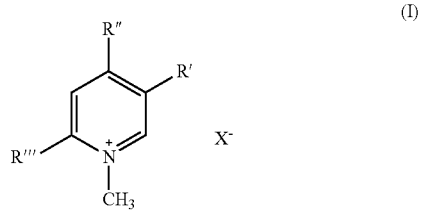

(I)

wherein R' is H, OH, $CONH_2$ or $COCH_3$, R" is H or $CH_3$, R''' is H or $CH_3$, and $X^-$ is a pharmaceutically acceptable counterion, in an amount sufficient to inhibit radiation-induced damage.

Without the intention of being bound by theoretical considerations, the present inventors believe that besides the compounds of formula (I) will possess the ability to reduce hypoxia in tumor cells. Hypoxia in tumor cells makes them more resistant to radiation therapy, and as a consequence substantially higher radiation dose is required to kill them. One of the proposed methods of overcoming this problem in the prior art was the use of oxygen/carbon dioxide breathing in combination with nicotinamide. However, very high dose of nicotinamide required (up to 6 g) and hepato- and gastrointestinal toxicity, as well as acute toxicity, i.e. mucosal and skin reactions, have been observed.

Contrary to other compounds used as radiosensitizers, compounds of formula (I) are active as radioprotectant at relatively low doses, are easy to administer to patients, provide high increase in tissue radiosensitization, while exhibiting little systemic toxicity and having low potential for causing skin/mucosa reactions. They are also freely accessible to all hypoxic cells within the tissue subjected to radiotherapy, such as tumor cells.

The term "a cell, tissue or organ damage" as used herein refers to any harmful effect that the ionizing radiation can exert on the living body. These effects include any acute effects and long-term effects of radiation poisoning, in particular organ dysfunction or failure, multiple organ failure and death. The term "radiation damage", whenever used herein, is meant to have the same meaning as the cell or tissue damage.

The term "prevention" means protection of a living subject from any harmful effect of the ionizing radiation, including the prevention of the radiation-induced death. The term includes also the protection against damage of normal cells and long-term consequences of such damage in a patient undergoing any type of radiotherapy, as well as a medical staff member involved in such radiotherapy.

The term "treatment" as used herein includes alleviation and/or relief or controlling the symptoms, reduction of severity of symptoms and restoring the health of the subject.

The invention can be especially advantageously used for the treatment with the view of prevention of radiation-induced lethality as an acute or long-term outcome of the radiation caused damage.

The term "living subject" which is protected and/or treated from radiation damage by the method of the invention is to be understood to include living organisms which were exposed in the past, are exposed or are expected to be exposed in the future to the action of the ionizing radiation. The term "subject" includes any human or animal such as a domestic or wild animal, particularly an animal of economic importance, such as a farm animal or a livestock. In a preferred embodiment, the term "living subject" refers to a human.

The term "living subject" includes, inter alia and without any limitations, the staff of industrial plants using ionizing radiation and/or radiation sources, people traveling and/or working in the outer space, medical professionals working in the field of radiodiagnostics and/or radiotherapy, patients undergoing radiotherapy, like radiotherapy of a cancer, inhabitants of the territories radioactively contaminated due to a nuclear attack or terroristic attack, the staff of rescue or emergency services, military staff, etc.

The term "ionizing radiation" as used herein refers to particles or waves having sufficiently high energy, typically the level of few eV being sufficient, to ionize an atom or a molecule in a living body. Waves radiation includes photon radiation, such as γ rays. Particle radiation includes the radiation of energy emitted in a form of electrically charged particles, such as α and β particles and protons. Particle radiation includes the radiation of energy emitted in a form of neutrons and neutrinos. Such particle radiation may be emitted by radioactive material, i.e. the material capable of emitting radioactive particles as a result of radioactive decay.

The radiation damage caused by ionizing radiation may result from the exposure to a radiation source, such as internal or external exposure.

Internal exposure may be caused by ingestion or inhalation of a material emitting ionizing radiation (radiation source), such as radioactive material. Such ingestion or inhalation can be accidental or intentional. Accidental ingestion or inhalation is also called a radiation-poisoning. Internal exposure may be caused as well by insertion or implantation of an radioactive material into a body, such as in the course of medical therapy. Such internal exposure may be chronic (long-term) or acute.

The term "external exposure to ionizing radiation" is meant to encompass the radiation that may be caused by natural or artificial (human-made) radiation sources. Natural ionizing radiation includes natural background radiation, like solar, cosmic or external terrestrial radiation. External terrestrial radiation includes the radiation emitted by naturally present radionuclides, as well as the human-made radiation. External terrestrial radiation includes the background radiation of the radon gas, which is emitted by the decay of radioactive radium and is present in the living environment.

Human-made radiation includes that emitted by industrial radioactive wastes, radioactively contaminated working or living environment, radiation sources and radioactive materials used in medicine and industry for diagnostic and measurement purposes, radiation sources used in medicine for therapeutic purposes.

In the field of medicine, especially encompassed are radiation sources used for eradication of cancers or tumors, and radiation sources used in nuclear medicine for diagnostic or therapeutic indications. In the case of diagnostic or therapeutic uses in medicine, whether accidental or intentional, the term "living subject" includes both patients and medical personnel.

Exposure to external ionizing radiation includes also any routine exposure to radiation in industrial plants, such as for example nuclear power stations or radioactive raw-materials mines.

Exposure to external ionizing radiation includes further any exposure during the outer space (cosmic) flights and expeditions.

Exposure to external ionizing radiation includes further any exposure to the radiation being a result of generally any hostile attack or the danger thereof with the use of nuclear weapon explosions and/or radioactive material poisoning, in particular a terrorist nuclear attack or the war attack resulting in the contamination of a living environment. In the case of a hostile attack the term "living subject" includes both civil targets/victims of the attack and the defense/rescue staff involved.

The term "radiotherapy", also called "radiation therapy", as used herein, is defined as any therapeutic use of ionizing high-energy from gamma rays, electrons, protons, neutrons, and other sources to kill cancer cells and shrink tumors. Radiation may come from a machine located outside the body (external-beam radiation therapy), or it may come from radioactive material placed in the body near cancer or tumor (internal radiation therapy, implant radiation, or brachytherapy).

External radiation therapy (radiation therapy using sources from outside the body), also called external-beam radiation, is a radiation therapy that uses a machine to aim high-energy rays at the cancer or tumor.

Internal radiation therapy (radiation therapy using radioactive materials placed inside the body) is a procedure in which radioactive material sealed in needles, seeds, wires, or catheters is placed directly into or near cancer or tumor.

The use of the compounds of the above formula (I) in any of the above radiation therapy procedures is contemplated and encompassed by the present invention.

In one aspect of the method of the invention, the compound of formula (I) is administered alone.

Generally, the compound of formula (I) can be also administered in combination with any other radioprotectants, including free-radical scavengers, such as for example amifostine and other aminothiole radioprotectants, vitamin E, vitamin C, selenium, melatonin, 5-androstenediol, curcumin, alpha-phenyl-tert-butylnitrone, a flavonoid, or a nitroxide.

The compound of formula (I) can be also administered in combination with any agent capable of removing radioactive substances from the body, such as radiogardase (prussian blue), pentetate calcium trisodium (Ca-DTPA) and pentetate zinc trisodium (Zn-DTPA).

The compound of formula (I) can be also administered in combination with any agent capable of inhibiting apoptosis, or growth factors, such as G-CSF and GM-CSF (filgrastim).

One group of the compounds of formula (I) which can be used in accordance with the present invention are those where in formula (I) R' is $CONH_2$ or $COCH_3$, R" is H and R''' is H.

Another group of the compounds of formula (I) which can be used in accordance with the present invention are those where in formula (I) one of R', R" and R''' is methyl, and the others are H atoms.

Particular compounds of formula (I) useful in the method of the present invention are selected from 1-methylnicotinamide, 1-methyl-3-acetylpyridinium, 1,2-dimethyl-pyridinium, 1,4-dimethylpyridinium, and 1,2,4-trimethylpyridinium salts.

Preferred salts include chloride, benzoate, salicylate, acetate, citrate and lactate. Especially preferred are chloride salts, due to physiological acceptability of the chloride anion.

Some of the compounds of formula (I) are commercially available, for example 1-methylnicotinamide chloride (from Sigma). Alternatively, the compounds can be readily prepared from commercially available compounds (including nicotinamide and nicotinic acid) by synthetic methods well-known to the person skilled in the art. Such methods would include synthesis from appropriately substituted pyridine compounds without methyl group at the pyridine nitrogen atom, i.e. in the position 1 of the pyridine ring. Quaternary pyridinium compounds of formula (I) wherein $X^-$ represents halogen anion can be prepared starting from corresponding pyridine compounds by direct methylation with methyl halogenide in a manner known per se. Quaternary pyridinium compounds of formula (I) wherein $X^-$ represents chloride anion can be prepared by direct methylation with methyl chloride, such as disclosed in AT131118, GB348345, U.S. Pat. No. 3,614,408, and U.S. Pat. No. 4,115,390. Quaternary pyridinium compounds of formula (I) wherein $X^-$ is a non-halogen anion can be prepared by substitution of a halogen anion to another anion, for example by treatment with a salt of such another anion, such as for example sodium or silver salt of another anion. As an illustration, lactates and acetates of the compounds of formula (I) can be prepared by the treatment of a halogenide, preferably chloride, with silver lactate or acetate, respectively. Salicylates of the compounds of formula (I) can be prepared by the treatment of a halogenide, preferably chloride, with sodium salicylate.

In the method of the invention the compounds of formula (I) can be administered orally or by injection, using any pharmaceutical dosage forms known for the person skilled in the art for such administration.

Preferred manner of administration is oral administration.

For oral administration both solid and liquid formulations can be used. Solid formulations include conventional tablets, capsules, troches, powders or granulates for direct ingestion or for reconstitution in liquids, such as water or juices. Any suitable conventional excipients can be used for the preparation of such solid forms. Liquid forms for oral administration include in particular aqueous solutions, with the addition of any conventional excipients, such as for example flavours and/or sweeteners.

Another preferred manner of administration is parenteral administration, especially by continuous infusion or a single bolus.

The administration by injection includes bolus intravenous injection, continuous intravenous infusion, as well as subcutaneous injection. Any suitable injections formulations can be used, such as for example aqueous saline solutions, buffered saline solutions, etc. using conventional excipients known from the art, such as preservatives, isotonic agents, buffers, etc.

The administration, in a single dose or in multiple doses can be prior or after each radiation episode and can be continued in cycles, such as everyday or every several days. The administration can be also continued after the radiation episode for several days or weeks. In the case of long-term radiation exposure the administration can be during the whole exposure period and can be continued after cessation of the exposure for several days or weeks.

Actual dosage levels of the compound of formula (I) in the method of this invention may be varied so as to obtain an amount of the active ingredient which is effective to achieve the desired therapeutic response for a particular patient, composition, and mode of administration, without being toxic to the patient.

Dosage regimen in the case of the administration as a protective measure in the case of the routine, expected or predictable long-term exposure to the low-dose ionizing radiation can be in the range of about 0.01 to 10 g of the compound of formula (I) per day. The compound can be administered as a protective measure before the onset to the exposure in one single dose, or alternatively in divided doses, during the period of such exposure and optionally for some period after cessation of the exposure. The administration can be preferably repeated every day.

In the case of expected acute exposure, such as for example the exposure of a professional rescue or emergency staff after accidents involving ionizing radiation, the compound should be administered prior the expected exposure, in one single dose or in multiple doses and preferably its administration should be continued for the whole period of exposure. In the case of accidental acute exposure, the compound should be administered to the victim of such accidental exposure as quickly as possible after the exposure had taken place and conveniently should be continued daily for some period, such as several days or weeks after the exposure. In such cases a dosage regimen of about 0.02 to 20 g per day is contemplated, depending on the radiation dose absorbed by the organism.

Dosage regimens in the case of administration as a part of a radiotherapy procedure can be in the range of about 0.02 to 20 g of the compound of formula (I) in a one single dose before irradiation, such as 1 hour, 30 minutes or 15 minutes before irradiation. In particular, dosages such as 5 mg to 20 g can be used, or 5 mg to 10 g, In some embodiments, a dose the compound of formula (I) is about 1 g, or about 2 g, or about 3 g, or about 4 g, or about 5 g, or about 6 g, or about 7 g, or about 8 g, or about 9 g, or about 10 g, or about 11 g, or about 12 g, or about 12 g, or about 13 g, or about 14 g, or about 15 g, or about 16 g, or about 17 g, or about 18 g, or about 19 g, or about 20 g.

Generally, the dose of the compound of the formula (I) shall be dependent on the absorbed or expected dose of the radiation. The selected dosage level will also depend upon a variety of factors including the activity of the particular compound of the present invention employed, the time of administration, the rate of excretion of the particular compound being employed, the duration of the treatment, other drugs, compounds or materials used in combination with the particular compound, the age, sex, weight, condition, general health and prior medical history of the patient being treated, and like factors well known in the medical arts.

A medical doctor, e.g., physician or veterinarian, having ordinary skill in the art can readily determine and prescribe the effective amount of the pharmaceutical composition required.

One of ordinary skill in the art would be able to study the relevant factors and make the determination regarding the effective amount of the therapeutic compound without undue experimentation.

The following examples are included to exemplify and illustrate the invention and its preferred embodiments.

EXAMPLES

The survival rate of irradiated mice treated with the compounds in comparison control was used as a measure of a radioprotective effect.

Example 1

Radioprotective Effect of 1-Methylnicotinamide Chloride

The methodology used was as described by Cheda et al., Radiation Research 2004, 161, 335 (animals and irradiation).

The survival rate of mice irradiated with lethal dose of about 7.5 Gy was tested. The treatment group received 1-methylnicotinamide chloride (MNA) in drinking water at an average dose of 300 mg/kg per day every day starting from the 7th day preceding the irradiation day. The administration was continued after irradiation. The control group received no treatment.

The effect of the prior administration of MNA on the survival rate of mice vs time after whole body irradiation with the dose of 7.5 Gy in comparison with control is shown in FIG. 1. As it can be seen, the survival rate of mice treated with MNA was clearly (statistically significant) higher than the survival rate of control mice and reaches about 50% as compared with approximately 20% of survival in untreated group of mice.

Example 2

The Effect of the Administration of 1-Methylnicotinamide Chloride (MNA), 1,4-Dimethylpyridinium Chloride (DMP), and 1-Methyl-3-Acetylpyridinium Chloride (MAP)

The methodology followed was as described in B Hou. Z. W. Xu, C. W. Yang, Y. Gao, S. F. Zhao, C. G. Zhang: Protective effects of inosine on mice subjected to lethal total-body ionizing irradiation. J Radiat Res 48, 57-62, 2007. In brief, six-to-eight-week old male BALB/c mice obtained from the Nofer Institute of Occupational Medicine, Łódź, Poland were used for the experiments. Whole bodies of the animals were exposed to a single irradiation (at the Military Institute of Chemistry and Radiometry) with gamma rays from the $^{60}$Co source at 7.2 Gy/h mean dose rate to obtain the absorbed dose of 7.5 Gy per mouse. The absorbed doses were verified using thermoluminescent dosimeters implanted subcutaneously in the middle abdominal region. All the mice were maintained under specific pathogen-free conditions. Survival of the mice was assessed during 30 days following the irradiation.

The mice were divided into irradiated control group receiving no treatment, irradiated treatment group receiving MNA, irradiated treatment group receiving DMP, and irradiated treatment group receiving MAP. Each of the treatment groups was divided into two subgroups, the first group in which the animals received the tested compounds starting from day 7 before the irradiation, and the second group in which the animals received the tested compounds starting from day 7 after the irradiation.

The compounds were given dissolved in drinking water at 100 mg/kg of body weight/24 h (DMP and MAP) and 500 mg/kg of body weight (MNA)/24 h until day 30 post irradiation.

Figure 2:
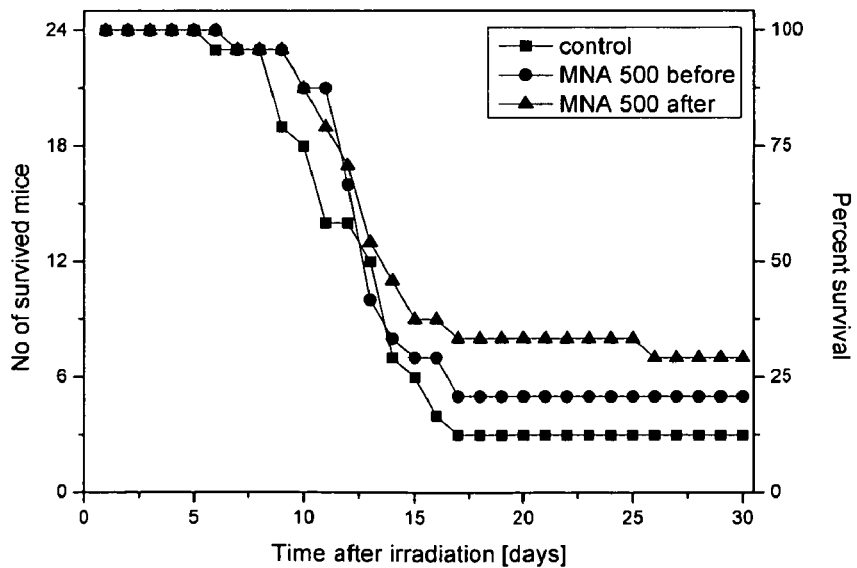
FIG. 2 shows the effect of the administration of 1-methylnicotinamide chloride (MNA) at 500 mg/kg/day given before or after irradiation on the survival rate of mice after whole body irradiation with the dose of 7.5 Gy in comparison with the untreated group of mice. The influence of MNA given before or after irradiation at 500 mg/kg/day on the mice survival following the whole body irradiation with the dose of 7.5 Gy
Figure 3:
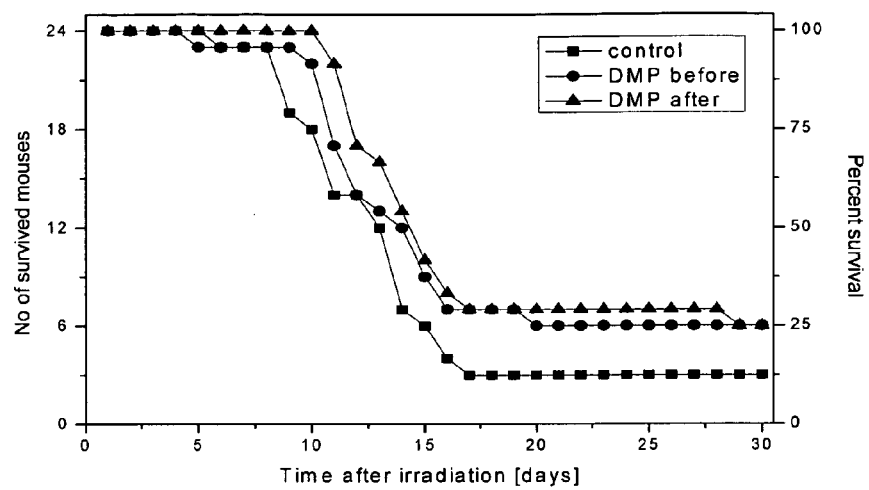
FIG. 3 shows the effect of the administration of 1,4-dimethylpyridinium chloride (DMP) at 100 mg/kg/day given before or after irradiation on the survival rate of mice after whole body irradiation with the dose of 7.5 Gy in comparison with the untreated group of mice. The influence of DMP given before or after irradiation at 100 mg/kg/day on the mice survival following the whole body irradiation with the dose of 7.5 Gy
Figure 4:
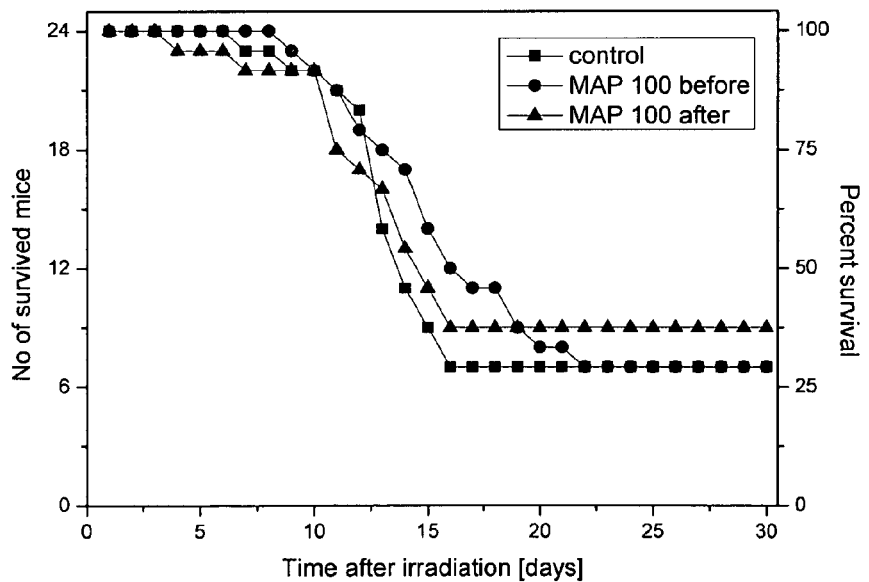
FIG. 4 shows the effect of the administration of 1-methyl-3-acetylpyridinium chloride (MAP) chloride at 100 mg/kg/day given before or after irradiation on the survival rate of mice after whole body irradiation with the dose of 7.5 Gy in comparison with the untreated group of mice. The influence of MAP given before or after irradiation at 100 mg/kg/day on the mice survival following the whole body irradiation with the dose of 7.5 Gy

The results of the tests are presented on FIG. 2 (MNA), FIG. 3 (DMP), and FIG. 4 (MAP). It can be seen that the compounds tested exert their protective activity both when administered prior irradiation and when administered after irradiation.

The invention claimed is:

1. A method for the treatment or inhibition of a cell or tissue damage in a living subject due to the exposure to ionizing radiation, which method comprises administration to said subject of a compound of formula (I)

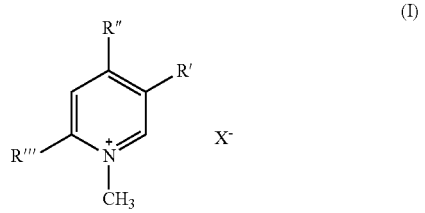

wherein R' is H, OH, CONH$_2$ or COCH$_3$, R" is H or CH$_3$, R''' is H or CH$_3$, and X— is a pharmaceutically acceptable counterion, in an amount sufficient to inhibit radiation-induced damage.

2. The method of claim 1 wherein said exposure is an accidental internal or external radiation exposure.

3. The method of claim 1 wherein said exposure is an acute high-dose internal or external radiation exposure.

4. The method of claim 1 wherein said exposure is a chronic internal or external radiation exposure.

5. The method of claim 1 wherein said subject is a patient undergoing external or internal radiotherapy.

6. The method of claim 1 wherein said subject is a medical professional involved in radiodiagnostics and/or radiotherapy.

7. The method of claim 1 wherein the compound of formula (I) is administered prior to the exposure of said subject to the radiation.

8. The method of claim 1 wherein the compound of formula (I) is administered after the exposure of said subject to the radiation.

9. The method of claim 1 wherein the compound of formula (I) is administered on a long-term basis before, during and/or after said exposure.

10. The method of claim 1 wherein in formula (I) R' is CONH$_2$ or COCH$_3$, R" is H and R''' is H.

11. The method of claim 1 wherein in formula (I) one of R', R" and R''' is methyl, and the others of R', R" and R''' are all H atoms.

12. The method of claim 1 wherein the compound of formula (I) is selected from l-methylnicotinamide, 1-methyl-3-acetylpyridinium, 1,2-dimethylpyridinium, 1,4-dimethylpyridinium, and 1,2,4-trimethylpyridinium salts.

13. The method of claim 1 wherein the compound of formula (I) is administered orally.

14. The method of claim 1 wherein the compound of formula (I) is administered parenterally.

15. The method of claim 1 wherein the compound of formula (I) is administered as a sole treatment.

16. The method of claim 1 wherein the compound of formula (I) is administered in combination with an agent accelerating removal of radioactive source from the body.

17. The method of claim 1 for the treatment of acute radiation sickness.

18. A method for the treatment of a cancer or tumor which comprises administration to a patient in need of such therapy of a compound of formula (I)

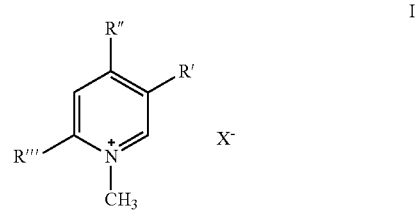

wherein R' is H, OH, CONH$_2$ or COCH$_3$, R" is H or CH$_3$, R''' is H or CH$_3$, and X$^-$ is a pharmaceutically acceptable counterion, in an amount sufficient to inhibit radiation-induced damage, and subjecting said patient to a radiotherapy procedure.

19. A method for inhibiting radiation-induced damage of a living subject in a need of such treatment which comprises administration to said subject prior, during or following the radiotherapy of a compound of formula (I)

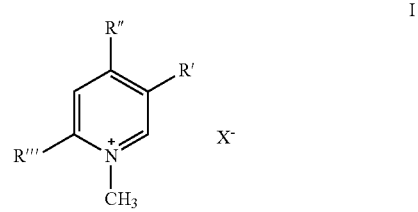

wherein R' is H, OH, CONH$_2$, COCH$_3$, and R" is H, CH$_3$, and R''' is H, CH$_3$, and X$^-$ is a pharmaceutically acceptable counterion.

* * * * *